US 8,536,357 B2

(12) United States Patent
Dietrich et al.

(10) Patent No.: US 8,536,357 B2
(45) Date of Patent: Sep. 17, 2013

(54) PROCESS FOR HETEROGENEOUSLY CATALYSED ESTERFICATION OF FATTY ACIDS

(75) Inventors: Wulf Dietrich, Cologne (DE); Dieter Heinz, Bergisch Gladbach (DE); Leslaw Mleczko, Dormagen (DE); Shaibal Roy, Cologne (DE); Heinrich Morhenn, Cologne (DE); Robert Tyron Hanlon, Philadelphia, PA (US)

(73) Assignee: Bayer Technology Services GmbH, Leverkusen (DE)

( * ) Notice: Subject to any disclaimer, the term of this patent is extended or adjusted under 35 U.S.C. 154(b) by 718 days.

(21) Appl. No.: 12/362,775

(22) Filed: Jan. 30, 2009

(65) Prior Publication Data
US 2009/0294358 A1 Dec. 3, 2009

Related U.S. Application Data

(63) Continuation-in-part of application No. PCT/EP2008/008762, filed on Oct. 16, 2008.

(30) Foreign Application Priority Data

Oct. 30, 2007 (DE) .......................... 10 2007 052 064
Feb. 1, 2008 (DE) .......................... 10 2008 007 431

(51) Int. Cl.
*C11B 3/02* (2006.01)
(52) U.S. Cl.
USPC .............................. 554/174; 554/30; 554/175

(58) Field of Classification Search
None
See application file for complete search history.

(56) References Cited

U.S. PATENT DOCUMENTS

| 4,698,186 A | * | 10/1987 | Jeromin et al. ................ 554/174 |
| 2005/0113589 A1 | * | 5/2005 | Katayama et al. ............. 554/174 |
| 2006/0293533 A1 | * | 12/2006 | Iyer .............................. 554/174 |

FOREIGN PATENT DOCUMENTS

| DE | 19600025 A1 | | 7/1997 |
| GB | 2145079 A | | 3/1985 |
| WO | 20061133437 A | | 12/2006 |
| WO | WO 2007/083213 | * | 7/2007 |

OTHER PUBLICATIONS

Gutsche et al, 1997, Prepartion of Fatty Acis with low acid values, useful as precursors for esterification reactions, DE 19600025 (English Translation), 4 pages.*
Canakci, M. et al., Biodiesel production from oils and fats wth high free fatty aics, 2001, ASAE, vol. 44, No. 6, pp. 1429-1436 (8 pages).*
Ecoscience Investments, Pty Ltd Eco-X Biodiesel Plant, Ecoscience Investments, 7 pages.*
English Language Abstract for DE 196 00 025.

* cited by examiner

*Primary Examiner* — Yate K Cutliff
(74) *Attorney, Agent, or Firm* — Norris McLaughlin & Marcus PA

(57) ABSTRACT

The invention relates to a process for esterifying free fatty acids in vegetable and animal fat with alcohols over heterogeneous acidic ion exchange resin catalysts at temperatures of 60 to 120° C.

19 Claims, 3 Drawing Sheets

PROCESS FOR HETEROGENEOUSLY CATALYSED ESTERIFICATION OF FATTY ACIDS

This application is a Continuation In Part Application of PCT/EP2008/008762 filed Oct. 16, 2008, which claims priority to the German application 10 2007 052 064.8 filed Oct. 30, 2007 and German Application 10 2008 007 431.4 filed Feb. 1, 2008.

FIELD OF THE INVENTION

The invention relates to a process for esterifying free fatty acids in vegetable and animal fat with alcohols over heterogeneous acidic ion exchange resin catalysts at temperatures of 60 to 120° C.

BACKGROUND OF THE INVENTION

Vegetable and animal fats and oils often contain considerable proportions of free fatty acids. The content of free fatty acids may be between 0 and 100% according to source of the fatty raw material. The proportion of free fatty acids cannot be reacted with methanol to give the corresponding fatty acid methyl esters in the preparation processes for biodiesel by transesterification of triglycerides with methanol and leads to yield losses or to the result that raw materials with a high content of free fatty acids are unsuitable for biodiesel production. A pretreatment of the fats is therefore necessary, in which the content of free fatty acids is reduced by conversion to fatty acid alkyl esters.

The literature discloses the esterification of the free fatty acids in fats or oils with methanol with the aid of a homogeneous acidic catalyst, for example p-toluenesulphonic acid. However, this process entails a relatively difficult catalyst removal, since the mineral acid catalyst has to be neutralised and removed with an immiscible liquid entrainer added actually before the esterification (E. Breitmaier and G. Jung, Organische Chemie I&II, Georg Thieme Verlag, 1994, 3rd edition, p. 271f(I); p. 490(II)).

EP 0192035 describes a process for deacidifying fats or oils, in which acidic solid ion exchange resins are used as catalysts, and whose removal from the reaction mixture is followed by removal of the water by-product. However, a high excess of methanol is required in this process to achieve a high conversion of the free fatty acids. For example, for a fatty acid conversion of 95%, a molar methanol to fatty acid ratio of 35:1 is required. For the distillative removal of the water by-product from the reaction product, the methanol used in excess likewise has to be evaporated owing to its lower boiling point, which causes a very high energy consumption.

According to EP 0192035 (Example 1), an addition of 0.2 l of methanol per 1 l of oil with an acid number of 10 (corresponds to a content of free fatty acids of 5% by weight) is required. In order to achieve a conversion of the free fatty acids of 90%, i.e. a reduction in the acid number from 10 to below 1, according to EP 0192035, an amount of catalyst of 7 liters per liter of oil per hour is needed, which gives rise to considerable reactor volumes and correspondingly high capital costs.

DE 19600025 describes a two-stage process for esterifying free fatty acids with heterogeneous catalysts analogously to EP 0192035, wherein the water by-product is removed between the two reaction stages and the amount of alcohol required is divided uniformly between the two reaction stages. When the esterification is used as a preliminary stage for a transesterification reaction with the same alcohol, this enables a reduction in the energy expenditure for the distillative removal of water and excess alcohol, since the alcohol can remain in the reaction mixture after the second reaction stage.

DE 19600025 further discloses that, in the case of the maximum esterification conversion of 90% disclosed, a maximum acid number of no more than 60 mgKOH/g may be present in the starting material (corresponds to a concentration of free fatty acids of approx. 30% by weight); this among other factors results in the calculated, only very low space-time yield of 34 g of fatty acid methyl ester per liter of reactor volume and hour in the disclosure according to DE 19600025. At a relatively low molar ratio of methanol to fatty acid of 17.5:1, only 85% fatty acid conversion is achieved.

A cause which can be cited for these disadvantages in DE 19600025 is the disclosure that operation of the process is possible only up to 70° C. using ion exchange resins, since there is thought to be a risk of inadequate stability of such a catalyst. For operation under temperatures higher than these, the use of silica gel-based catalysts is proposed, but these appear disadvantageous for the following reasons.

Under some circumstances, all catalysts exhibit the phenomenon of leaching, which is known to those skilled in the art and encompasses the discharge of catalyst material into the product. It is advantageous in this context when the catalyst consists of substances which are at least chemically similar to the starting materials, or products of the process within which it is used, in order that contamination of the product by leaching has a lesser adverse effect on the product quality. In connection with the preparation of alkyl esters, the use of hydrocarbon-based catalysts, which also include the ion exchange resins, is thus advantageous.

The person skilled in the art is also aware that increasing the temperature generally increases the reaction rate of a chemical reaction and hence, within a given time, an increased, economically advantageous conversion to product can be achieved. DE 19600025, however, points out the inadequate thermal stability of the ion exchange resin catalysts and the use of other heterogeneous acidic catalysts in applications under high temperatures.

For an economically viable and energetically optimal esterification of free fatty acids in vegetable and animal fats and/or oils with alcohols for biodiesel production, it is thus an object of the invention to develop a process which reduces the content of free fatty acids to the demands of a downstream transesterification stage, by virtue of the reaction achieving a high conversion of the free fatty acids at elevated temperatures and very low alcohol excess, such that the process enables an improvement in the space-time yield and hence in the required apparatus size as compared with the prior art processes.

SUMMARY OF THE INVENTION

It has been found that, surprisingly, the above object is achieved by a process for reducing the content of free fatty acids in starting materials, characterized at least by the steps of
1) reacting the free fatty acids with alcohols at temperatures between 60 and 120° C. using acidic, heterogeneous ion exchange resin catalysts,
2) optionally removing water, and optionally alcohol at least partly together with it,
3) optionally further reacting the free fatty acids with alcohols at temperatures between 60 and 120° C. using acidic, heterogeneous ion exchange resin catalysts.

DETAILED DESCRIPTION OF THE INVENTION

Useful starting materials for the process according to the invention include all fats and oils whose content of free fatty acids by nature is not sufficiently low that they can be supplied without esterification directly to further processing by transesterification of the fatty acid glycerides present therein by a customary process known to those skilled in the art.

Nonexclusive examples of natural fats and oils are coconut oil, palm oil, palm kernel oil, cottonseed oil, rapeseed oil, groundnut oil, olive oil, linseed oil, babassu oil, tea oil, olive kernel oil, meadowfoam oil, chaulmoogra oil, coriander oil, soya oil, castor oil, lard oil, bovine tallow, pork lard, fish oil, jatropha oil, recycled cooking oils, fatty substances from algae, and sunflower oil. In addition to the natural fats and oils, it is also possible to use synthetic fats and oils. These are obtained, for example, by at least partial esterification of glycerol with fatty acids.

Preferred starting materials are vegetable fats, animal fats, vegetable oils and/or animal oils, especially palm oil, palm fatty acid distillates (PFAD), jatropha oil, recycled fats from used cooking oils and/or wastewater cleaning, and bovine tallow and poultry grease.

In the context of the present invention, the term "fatty acid glycerides" should be understood to mean all glycerides of fatty acids, i.e. both fatty acid triglycerides and corresponding fatty acid partial glycerides, such as mono- and diglycerides, and mixtures thereof.

In the context of the present invention, fatty acids are understood to mean aliphatic carboxylic acids of the formula (I):

$$R^1CO-OH \qquad (I)$$

in which $R^1$ is an aliphatic, linear or branched carbon radical having 6 to 22 carbon atoms and optionally one or more double bonds. Nonexclusive examples thereof are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, eleostearic acid, arachic acid, gadoleic acid, behenic acid and erucic acid, and technical mixtures thereof.

The acid number of the starting material in the process according to the invention may be up to 200 mg KOH/g, preferably 5 to 60 mg KOH/g and more preferably 10 to 40 mg KOH/g.

In this connection, the acid number indicates the mass of potassium hydroxide in mg which is required to neutralize 1 g of the sample to be studied (DIN 53402, newest version DIN EN ISO 2114).

The inventive acidic, heterogeneous ion exchange resin catalysts are preferably strongly acidic polymeric macroporous resins with free sulphonic acid groups.

The ion exchange resin catalysts used preferably have an activity of at least 0.1 kg of free acid per kg of catalyst. This activity is particularly advantageous because it ensures that the process according to the invention is performable reliably with the advantageous catalyst hourly space velocities in step 1) and/or 3).

Likewise preferably, the acidic, heterogeneous ion exchange resin catalyst is present in particles or particle beds, the particles more preferably having a diameter between about 0.5 mm and 1 mm.

When particle beds are used, they are used preferably in the form of a fixed bed. Preference is given to configuring the particle bed in the form of a fixed bed such that the fixed bed, using the above-described catalyst particles, has a pressure drop of not more than 0.5 bar/m.

Preferred lengths of such a fixed bed in the form of a particle bed are between 1 and 10 m.

The person skilled in the art is aware of suitable methods of achieving the properties of fixed beds just mentioned. Nonexclusive examples include suitable compacting of the bed, or use of guide plates in the bed.

It has likewise been found that, surprisingly, the Amberlyst® ion exchange resin catalysts from Rohm and Haas and the Lewatit® ion exchange resin catalysts from Lanxess are especially preferred since, contrary to the information in the prior art, they can be used at the higher temperatures in accordance with the invention during the performance of the process according to the invention.

Preferred alcohols in the process according to the invention are monohydric or polyhydric $C_1$ to $C_5$ alcohols or mixtures thereof. In the context of the present invention, the hydricity of an alcohol describes the number of hydroxyl groups covalently bonded to carbon in the alcohol. Nonexclusive examples of monohydric, preferred alcohols are butanol, isopropanol, propanol, ethanol and/or methanol. In addition, it is also possible to use water-soluble polyols, for example ethylene glycol and/or glycerol. Particular preference is given to methanol.

The alcohol is used in step 1) of the process according to the invention preferably in a molar excess based on the free fatty acids of 5 to 40. In a particularly preferred embodiment, the alcohol is added to the starting material in a molar ratio of 5 to 20, most preferably of 10 to 20.

The reaction of the free fatty acids in step 1) of the process according to the invention is carried out preferably at temperatures between 80 and 95° C.

Likewise preferably, step 1) of the process according to the invention is carried out at elevated pressure relative to ambient pressure (1013 hPa). Particular preference is given to selecting the pressure of the process according to the invention in step 1) such that it corresponds at least to the vapour pressure of the alcohol used under the other process conditions. The vapour pressures of the inventive alcohols under various ambient conditions are known to those skilled in the art, or are tabulated in the VDI Wärmeatlass or similar reference works. Very particular preference is given to using pressures below 5 bar.

The preferred pressures are advantageous because this prevents alcohol from escaping from the reaction mixture through evaporation during the conversion. It is thus available in a maximum amount during the conversion, such that the desired space-time yields are achieved. An increase above the magnitude of 5 bar is only disadvantageous because this prevents the necessity of using specialized pressure vessels to perform the process according to the invention. The specialized pressure vessels are more expensive as a result of their specialized design and are therefore disadvantageous under some circumstances in the context of the economic viability of the process.

Likewise preferably, step 1) of the process according to the invention is performed such that the reaction time of the free fatty acids with the alcohol does not exceed 30 minutes. This means that fluid elements, on average, remain only for a time of less than or equal to 30 minutes in the reaction zone in step 1).

The reaction time can be established, for example, by passing the free fatty acids and the alcohol over the acidic ion exchange resin catalyst at a particular rate.

The preferred reaction time is advantageous because it has been found in the process according to the invention that this time constitutes the limit within which high conversions of the free fatty acids can already be achieved, such that a further increase in the reaction time can no longer positively influence the space-time yield achieved any further. In addition, it has been found that this limit is independent of the entry concentration of the free fatty acids.

In a further preferred embodiment of step 1) of the process according to the invention, the process is operated such that a particular catalyst hourly velocity of the acidic, heterogeneous ion exchange resin catalyst is established. This is preferably established as a function of the acid number of the starting material.

In connection with the present invention, catalyst hourly space velocity refers to the mass of free fatty acid per unit mass of acidic, heterogeneous ion exchange resin catalyst and time, expressed in $$\frac{kg}{kg \cdot h}.$$

The catalyst hourly velocity established may generally be $$0.1 \text{ to } 10 \ \frac{kg}{kg \cdot h},$$

preferably $$0.15 \text{ to } 5 \ \frac{kg}{kg \cdot h},$$

more preferably $$0.2 \text{ to } 3 \ \frac{kg}{kg \cdot h}.$$

When a starting material with an acid number less than or equal to 40 by the above definition is used, a catalyst hourly space velocity of $$0.1 \text{ to } 4 \ \frac{kg}{kg \cdot h}$$

is preferred. Particular preference is then given to a catalyst hourly space velocity of $$0.15 \text{ to } 2.5 \ \frac{kg}{kg \cdot h}.$$

Very particular preference is then given to a catalyst hourly space velocity of $$0.2 \text{ to } 1.6 \ \frac{kg}{kg \cdot h}.$$

When a starting material with an acid number greater than 40 by the above definition is used, a catalyst hourly space velocity of $$0.3 \text{ to } 10 \ \frac{kg}{kg \cdot h}$$

is preferred. Particular preference is then given to a catalyst hourly space velocity of $$0.4 \text{ to } 5 \ \frac{kg}{kg \cdot h}.$$

Very particular preference is then given to a catalyst hourly space velocity of $$0.5 \text{ to } 3 \ \frac{kg}{kg \cdot h}.$$

A lower catalyst hourly space velocity is inefficient in each case, since more free fatty acid could be converted and hence the aim of a high space-time yield has not been met. A higher catalyst hourly space velocity leads to no longer sufficient conversions of the free fatty acids and hence also to lower space-time yields.

The catalyst hourly space velocity can be set via adjustment of the mass flow of the free fatty acids, or adjustment of the amount of catalyst.

In a preferred development of step 1) of the process, the acidic, heterogeneous ion exchange resin catalyst in the reaction zone is present in a continuous alcoholic phase in which the free fatty acids are finely dispersed.

Means of achieving a fine dispersion of one phase in another include construction measures within and/or upstream of the reaction zone, for example in the form of internals which promote specific phase conditions (perforated plates, static mixers, nozzles, etc.), but also process technology measures, for instance changes in the flow regime in the reaction zone.

Preference is given to process technology measures. A particularly preferred measure is that the reaction zone in which the conversion is performed is flowed through vertically from the top downward.

In the preferred development, the reaction mixture, at the entrance to the reaction zone, is a biphasic mixture of fatty acids and alcohol, the density of the alcoholic phase generally being lower than that of the fatty acid phase. As a result of the density difference, fractions of the alcoholic phase thus collect at the upper end of the reaction zone in the course of stable operation of the process in its preferred development. As a result of the flow through the reaction zone, these are subsequently entrained vertically from the top downward through the reaction zone, such that the alcoholic phase always forms the continuous phase in which the fatty acid phase is present in finely dispersed form. This process technology measure therefore allows, in a particularly advantageous and simple manner, the establishment of a continuous alcoholic phase in which the fatty acid phase is present in finely dispersed form.

It has now been found that, surprisingly, the alcoholic phase has a significantly better wetting capacity of the catalyst used than the fatty acid phase, as a result of which an operation in which the alcohol forms a continuous phase in which the fatty acid is present in finely dispersed form allows the physical properties of the two phases to be exploited in an optimal manner. This allows particularly intensive contact of the reaction mixture with the catalyst surface to be achieved.

In connection with the present invention, a fine dispersion means the presence of droplet sizes of the fatty acid phase in the alcohol phase of, on average, not more than 2 mm. This fine dispersion leads to a more homogeneous loading of the catalyst in the reaction zone with the two phases, which in turn leads to enhanced yields.

The advantages which have surprisingly been found, in conjunction with the phase ratio in the reaction zone, according to the preferred development of step 1) of the process, make it possible to reduce the temperatures at which the reaction is performed, without having to accept a significant loss in the conversion achieved. This in turn causes reduced energy inputs into the process, which is economically advantageous.

The process according to the invention in the preferred development of step 1) is advantageous since the conversion based on the proportion of free fatty acids is already greater than 98.0%, and so the object of improving the space-time yield is thus achieved.

The process according to the invention and its preferred developments can be performed with or without removal of water in step 2). Preference is given to performing a removal of water and if appropriate alcohol at least partly together therewith.

When removal of water in step 2) of the process according to the invention is desirable, in this preferred process variant, the stream obtained therefrom is either sent to further processing by a transesterification of the triglycerides by a customary process known to those skilled in the art or, if appropriate, to a further conversion in step 3) of the process according to the invention.

Preference is given to performing step 2) of the process according to the invention such that only water is removed, in order that any as yet unconverted alcohol is still available to further processing by a transesterification or further conversion in step 3) of the process according to the invention, and the process thus leads to an increased space-time yield for the purposes of achieving the object.

Possible methods of removing water and, if appropriate, alcohol at least partly together with it include, as nonexclusive examples, distillation, rectification, evaporation or membrane processes, whose suitable embodiments are known to those skilled in the art.

Particular preference is given to selective removal of water with the aid of a membrane. Very particular preference is given to selective removal by means of a hydrophobic membrane, for example commercially available microporous polypropylene membranes.

Likewise particularly preferred is removal of the water in step 2) of the process according to the invention together with a portion or the entirety of the alcohol by evaporation. This is particularly advantageous because the apparatus design is particularly simple and hence the costs of the process can be reduced, such that it becomes more economically viable.

When a further conversion of the free fatty acids in step 3) of the process according to the invention is desired, this preferred process variant can be carried out with or without further addition of alcohol. Preference is given to adding alcohol once again to the further conversion in step 3) of the process according to the invention. Particular preference is given to adding, in step 3), an amount of alcohol less than or equal to the amount of alcohol in step 1). Very particular preference is given to adding, in step 3), an amount of alcohol which corresponds exactly to that which has been converted and/or removed in the preceding steps 1) and if appropriate 2).

Likewise preferred is a performance of step 3) of the process according to the invention under the correspondingly preferred conditions with regard to temperature and/or pressure and/or residence time and/or catalyst hourly space velocity, as have been specified in step 1) of the process according to the invention.

In a preferred development of the process according to the invention, step 3) is performed in such a way that, in the reaction zone in which the further conversion is performed, the acidic, heterogeneous ion exchange resin catalyst is present in a continuous alcoholic phase in which the free fatty acids are present in finely dispersed form.

Analogously to the preferred development of step 1), as has already been described above, it is also possible here, through such an operation of the process, to achieve better wetting of the catalyst and hence to achieve an increased conversion. For step 3) of the process, this is particularly advantageous, since, especially in the case of a further conversion, the wetting and homogeneous loading of the catalyst are particularly important. This is caused by the fact that, at the entrance to the reaction zone of step 3), the proportion of starting material in the stream is lower than in step 1) of the process. According to principles which are common knowledge to those skilled in the art, the expected conversion under otherwise identical operating conditions is thus less than before. It is thus necessary to achieve maximum wetting in order to achieve advantageous conversions for the purposes of the desired space-time yield. This is enabled by such an operation in the manner described above.

As is also the case in the preferred development of step 1) of the process, preference is given to process technology measures in order to ensure a fine dispersion of the fatty acid phase in the alcoholic phase. It is a particularly preferred measure that the reaction zone in which the further conversion is performed is flowed through vertically from the top downward.

If it is desired to increase the conversion further, preference is given to performing step 3) more than once. Particular preference is given to performing the sequence of step 2) and step 3) of the process according to the invention more than once.

The process according to the invention in the preferred development of step 3) is advantageous since a conversion based on the free fatty acids in the starting material before performance of the first esterification reaction of more than 99.7% is achieved, and so the object of achieving an improvement in the space-time yield is thus achieved.

A very particularly preferred variant of the process according to the invention comprises all steps 1) to 3), wherein water, optionally together with alcohol, is removed in step 2) and the alcohol converted and/or removed in step 1) and/or step 2) is added again in such an amount that the same molar ratio of alcohol based on the amount of fatty acid originally supplied to the process as in step 1) is re-established.

All processes according to the invention, or preferred embodiments thereof or preferred individual steps thereof, can be performed continuously or batchwise. Preference is given to performing at least step 1), preferably step 1) and step 3), of the process according to the invention and each preferred variant thereof continuously with a fixed bed reactor. In this case, the fixed bed reactor more preferably comprises a bed of catalyst particles through which starting materials and alcohol(s) flow continuously. In this connection, "continuous" describes more particularly the non-batchwise conversion and/or removal of the substances by the inventive steps.

When the process according to the invention in steps 1) and/or 3), in a preferred embodiment, is performed continuously, the preferred reaction time specified for these steps should be equated to the residence time of the starting material and/or alcohols in this process step (for example in a fixed bed reactor).

By virtue of the process according to the invention and its preferred variants, it is possible for the first time to perform the esterification of free fatty acids in vegetable and animal fats and/or oils using a heterogeneous acidic ion exchange resin catalyst with a high space-time yield at a low alcohol excess for any concentrations of free fatty acids.

The surprising finding that it is possible to increase the reaction temperature enables a significant acceleration of the reaction and hence a substantial rise in the space-time yield by factors of about 5 to 20 compared to the prior art. In industrial-scale implementation, this corresponds to an approximately corresponding reduction in the reactor volume required and thus results in an economic advantage.

A further advantage of the process according to the invention arises through the reduction of the alcohol excess required.

In industrial application, approximately halving the amount of methanol required enables a reduction in the energy requirement for methanol removal of 3.28 MJ per kg of free fatty acid which is supplied to the esterification (in a typical industrial plant with a capacity of 12.5 t/h of oil with an acid number of 25, this corresponds to an energy saving of 0.9 MW).

For biodiesel production, this enables significantly less expensive processing of fatty raw materials with a high proportion of free fatty acids compared to the prior art processes and thus opens up a larger and less expensive spectrum of fatty raw materials.

Preferred embodiments of the process according to the invention will be illustrated in detail hereinafter with reference to drawings, without restricting them thereto.

Figure 1:
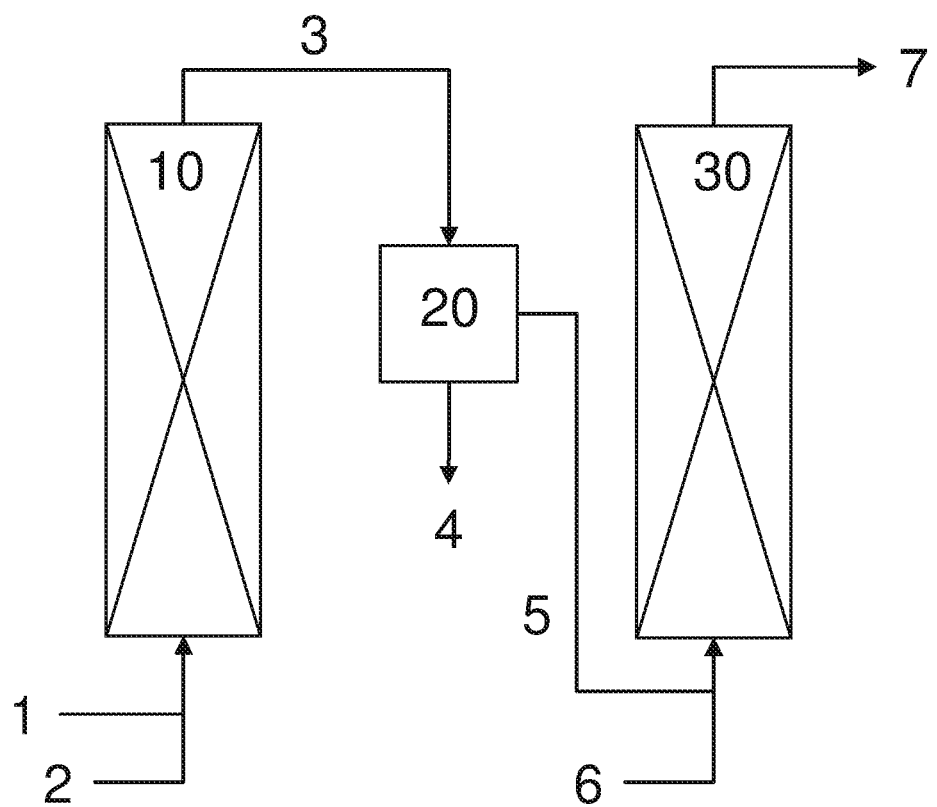
FIG. 1 shows a diagram of a particularly preferred embodiment. The starting material (1) is supplied continuously with the alcohol (2) to the first reaction stage (10) in step 1) of the process according to the invention. The reaction stage consists of a flow tube reactor which comprises a fixed bed consisting of a bed of catalyst particles (particle diameter 0.5 to 1 mm) with a length of 1 to 10 m. The diameter of the fixed catalyst bed is calculated from the volume flow of streams (1) and (2) such that the mean residence time of these two streams in the catalyst bed is 5 to 30 min. The superficial linear flow velocity of the liquid phase is 1 to 5 mm/s and the pressure drop due to friction in the particle bed is less than 0.5 bar/m. The conversion of free fatty acids at the exit from the first reaction stage is, for example, about 95%. From the product stream (3), the water by-product and the excess alcohol are evaporated in a separating stage (20) and removed as stream (4). The separating stage may, for example, be a falling-film evaporator or a distillation column which is operated at atmospheric or reduced pressure. After the separation stage, stream (5) is essentially anhydrous and is mixed with further alcohol (6) and supplied to a further reaction stage (30). In terms of its construction, this reaction stage corresponds to reaction stage (10). The conversion of free fatty acids at the exit from the second reaction stage (corresponds to stream (7)) is, for example, about 90% based on the starting material (5) of the second reaction stage and, for example, about 99.5% based on the starting material (1) of the first reaction stage.
Figure 2:
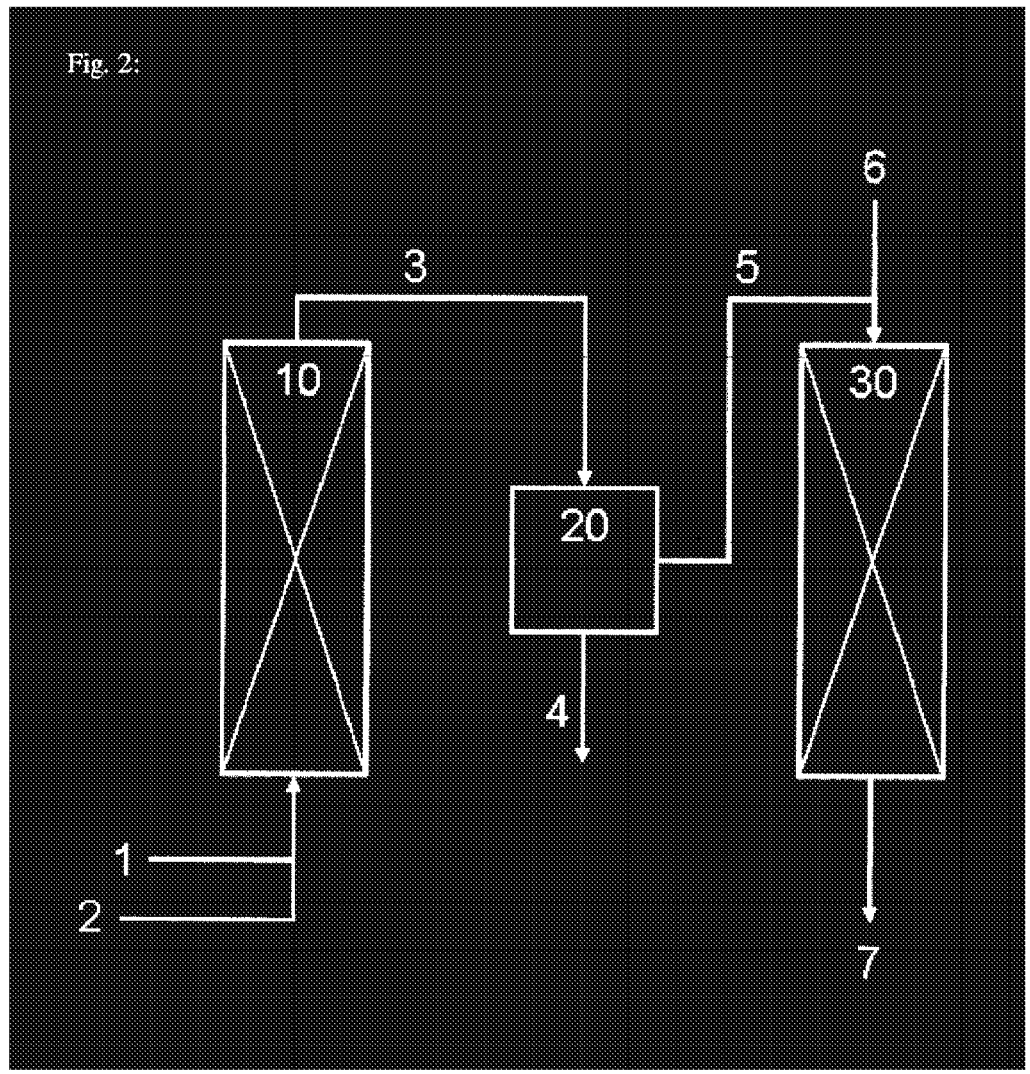
FIG. 2 shows a diagram of a particularly preferred embodiment. The starting material (1) is supplied continuously from the bottom with the alcohol (2) to the first reaction stage (10), in step 1) of the process according to the invention. The reaction stage consists of a flow tube reactor which comprises a fixed bed consisting of a bed of catalyst particles (particle diameter 0.5 to 1 mm) with a length of 1 to 10 m. The diameter of the fixed catalyst bed is calculated from the volume flow of streams (1) and (2) such that the mean residence time of these two streams in the catalyst bed is 5 to 30 min. The superficial linear flow velocity of the liquid phase is 1 to 5 mm/s and the pressure drop due to friction in the particle bed is less than 0.5 bar/m. The conversion of free fatty acids at the exit from the first reaction stage is, for example, about 95%. From the product stream (3), the water by-product and the excess alcohol are evaporated in a separating stage (20) and removed as stream (4). The separating stage may, for example, be a falling-film evaporator or a distillation column which is operated at atmospheric or reduced pressure. After the separation stage, stream (5) is essentially anhydrous and is mixed with further alcohol (6) and supplied to a further reaction stage (30) from the top, such that the reaction zone is flowed through vertically from the top downward. In terms of its construction, this reaction stage corresponds to reaction stage (10). The conversion of free fatty acids at the exit from the second reaction stage (corresponds to stream (7)) is, for example, about 90% based on the starting material (5) of the second reaction stage and, for example, about 99.7% based on the starting material (1) of the first reaction stage.
Figure 3:
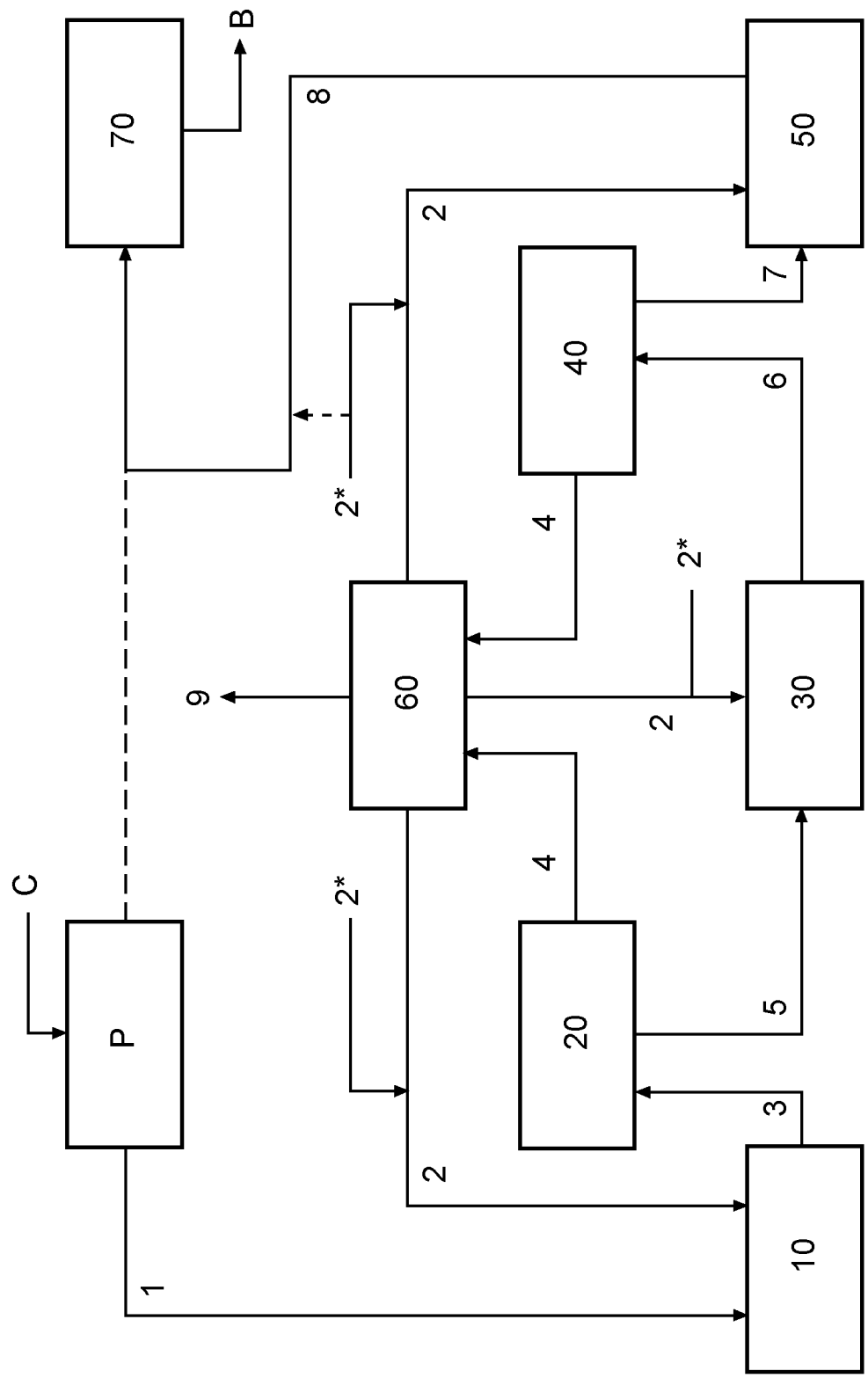
FIG. 3 shows a diagram of a further particularly preferred embodiment of the present invention. Therein a starting material (1) is fed into a first reaction stage (10), which results from crude material (C) having been pre-treated in a pre-treatment unit (P), which comprises the steps of degumming and bleaching as known from the prior art. The starting material (1) is fed into the first reaction stage (10) together with alcohol (2), which might be derived from a source of fresh alcohol (2*) or from a alcohol recovery unit (60), such as a distillation unit, from which a stream of water (9) is withdrawn for further use. The flow pattern in the first reaction stage (10) may be chosen such that the reaction zone is flowed through vertically from the bottom upward, as illustrated in the second reaction stage of previous FIG. 1 or vertically from the top downward, as illustrated in the second reaction stage of previous FIG. 2. From the first reaction stage (10) a stream of a first esterified product (3) is withdrawn and fed into a first separating stage (20), which can be of any kind illustrated previously by this invention. From said first separation stage (20) a stream of an alcohol/water mixture (4) is withdrawn and fed into the alcohol recovery unit (60) for further purification of the alcohol. An alcohol/water depleted stream (5) is withdrawn from the first separating stage (20) and fed into a second reaction stage (30) together with additional alcohol (2) from the alcohol recovery unit (60) or from a source of fresh alcohol (2*). Said second reaction stage (30), can again have any of the aforementioned flow patterns. After further esterification in the second reaction stage (30) a second esterified product (6) is withdrawn and fed into a second separating stage (40), which again can be of any kind illustrated previously by this invention and from which another stream of an alcohol/water mixture (4) is withdrawn and fed into the alcohol recovery unit (60) for further purification of the alcohol. Furthermore another alcohol/water depleted stream (7) is withdrawn from the second separating stage (40) and fed into a third reaction stage (50) together with additional alcohol (2) from the alcohol recovery unit (60) or from a source of fresh alcohol (2*). From the third reaction stage (50), which again can be designed to have any of the aforementioned flow patterns, a final reaction product (8) is withdrawn and fed into a biodiesel production process (70), known from the prior art, optionally together with additional alcohol (2*). From said biodiesel production process biodiesel (B) can be withdrawn as a final product of high quality as of no longer comprising free fatty acids. Optionally the product of the pre-treatment unit (P) may be partially fed into the biodiesel production process (70) directly, if the amount of free fatty acids in the aforesaid crude material is low, or if the quality of the resulting biodiesel (B) is not requested to be high.

The invention is illustrated in detail below with reference to the examples, but without restricting it to them.

EXAMPLES

Example 1

Conversion of Free Fatty Acids 1120 g/h of a mixture of rapeseed oil, oleic acid and linoleic acid with a content of free fatty acids of 12.5% by weight (corresponds to an acid number of approx. 25 mg KOH/g) was passed with 267 g/h of methanol at a temperature of 83° C. and a pressure of 4 bar with a residence time of 10 min over a fixed catalyst bed composed of 650 ml of acidic ion exchange resin (corresponds to 121 g of catalyst mass (dry)). The catalyst particles had a diameter of 0.8 mm and were immobilized in a fixed bed reactor with a catalyst bed length of 2.08 m. This gives rise to a catalyst hourly space velocity of 1.16 kg of free fatty acid per kg of catalyst and hour, and a superficial velocity of 3.5 mm/s. In the reaction product, an acid content of 0.21% by weight was determined.

A conversion of 98.3% with a molar ratio of methanol to fatty acids of 16.8:1 was thus achieved. This gives rise to a space-time yield of fatty acid methyl ester of 214 g per liter of reaction volume and hour.

Example 2

Conversion of Free Fatty Acids 379.5 g/h of a mixture of rapeseed oil, oleic acid and linoleic acid with a content of free fatty acids of 49% by weight (corresponds to an acid number of approx. 98 mg KOH/g) was passed with 474 g/h of methanol at a temperature of 83° C. and a pressure of 4 bar with a residence time of 15 min over a fixed catalyst bed composed of 650 ml of acidic ion exchange resin (corresponds to 121 g of catalyst mass (dry)). The catalyst particles had a diameter of 0.8 mm and were immobilized in a fixed bed reactor with a catalyst bed length of 2.08 m. This gives rise to a catalyst hourly space velocity of 1.54 kg of free fatty acid per kg of catalyst and hour, and a superficial velocity of 2.3 mm/s. In the reaction product, an acid content of 1.27% by weight was determined, i.e. a fatty acid conversion of 97.4% was achieved.

Example 3

Conversion and Further Conversion of Free Fatty Acids—Flow from the Top 740 g/h of a mixture of rapeseed oil, oleic acid and linoleic acid with a content of free fatty acids of 15.4% by weight (corresponds to an acid number of approx. 31 mg KOH/g) were passed with 242 g/h of methanol at a temperature of 83° C. and a pressure of 4 bar with a residence time of 15 min over a fixed catalyst bed composed of 650 ml of Amberlyst®BD20 acidic ion exchange resin (corresponds to 121 g of catalyst mass (dry)). The catalyst particles had a diameter of 0.8 mm and were immobilized in a fixed bed reactor with a catalyst bed length of 2.08 m and a diameter of 20 mm. In the reaction product, an acid content of 0.48% by weight was determined, i.e. a fatty acid conversion of 97% was achieved. The content of water which was formed as a by-product in the reaction was 0.23% by weight in the reaction product.

The reaction product was collected in a collecting vessel and transferred to a rotary evaporator. With the aid of the rotary evaporator, the unconverted methanol and water were removed by vacuum distillation. After the vacuum distillation, a water content of 0.04% by weight in the distillation residue was determined.

From the distillation residue, 1098 g/h together with 290 g/h of methanol were passed at a temperature of 83° C. and a pressure of 4 bar with a residence time of 10 min over a fixed catalyst bed composed of 650 ml of Amberlyst®BD20 acidic ion exchange resin (corresponds to 121 g of catalyst mass (dry)). The catalyst particles had a diameter of 0.8 mm and were immobilized in a fixed bed reactor with a catalyst bed length of 2.08 m and a diameter of 20 mm. The reaction mixture was supplied from the top, and so the reaction zone was flowed through vertically from the top downward. The superficial velocity of the reaction mixture was 1.39 mm/s. On entry into the reactor, the reaction mixture was supplied through a nozzle which, at the narrowest cross section, had a circular orifice with a diameter of 0.5 mm.

In the case of such a procedure in the further conversion, it was possible to observe formation of a continuous methanol phase in the top region of the reactor, in which oil droplets were present in dispersed form. This was clearly identifiable with reference to the speed of descent of the droplets of the disperse phase. At a mean droplet diameter of approx. 2 mm, a speed of descent of approx. 28 mm/s was measured, which was thus significantly greater than the mean superficial velocity of the reaction mixture, and so it was concluded from this that the droplets are oil which, under the experimental conditions, has a significantly higher density than methanol.

In the reaction product, after removal of the methanol, an acid content of 0.07% by weight was determined. A conversion, based on the free fatty acids at the entrance to the reaction zone for the further conversion, of 87.8% was achieved.

Overall, a total fatty acid conversion of 99.6% is calculated.

Example 4

Further Conversion at Lower Temperatures—Flow from the Top

From the distillation residue of Example 3, 730 g/h together with 192 g/h of methanol were passed at a temperature of 65° C. and a pressure of 4 bar with a residence time of 15 min over a fixed catalyst bed composed of 650 ml of Amberlyst®BD20 acidic ion exchange resin (corresponds to 121 g of catalyst mass (dry)). The catalyst particles had a diameter of 0.8 mm and were immobilized in a fixed bed reactor with a catalyst bed length of 2.08 m and a diameter of 20 mm. The reaction mixture was supplied from the top, and so the reaction zone was flowed through vertically from the top downward. The superficial velocity of the reaction mixture was 0.92 mm/s. On entry into the reactor, the reaction mixture was supplied through a nozzle which, at the narrowest cross section, had a circular orifice with a diameter of 0.5 mm.

In the reaction product, after removal of the methanol, an acid content of 0.05% by weight was determined. A conversion, based on the free fatty acids at the entrance to the reaction zone for the further conversion, of 89.8% was achieved.

Overall, a total fatty acid conversion of 99.7% is calculated.

Example 5

Conversion and Further Conversion of Free Fatty Acids—Flow from the Bottom

From the distillation residue of Example 1, 730 g/h together with 192 g/h of methanol were passed at a temperature of 83° C. and a pressure of 4 bar with a residence time of 15 min over a fixed catalyst bed composed of 650 ml of Amberlyst®BD20 acidic ion exchange resin (corresponds to 121 g of catalyst mass (dry)). The catalyst particles had a diameter of 0.8 mm and were immobilized in a fixed bed reactor with a catalyst bed length of 2.08 m and a diameter of 20 mm. The reaction mixture was supplied from the bottom, and so the reaction zone was flowed through vertically from the bottom upward. The superficial velocity of the reaction mixture in the reactor was 0.92 mm/s. On entry into the reactor, the reaction mixture was supplied through a nozzle which, at the narrowest cross section, had a circular orifice with a diameter of 0.5 mm.

In the case of such a procedure in the further conversion, it was possible to observe that a continuous oil phase formed in the bottom region of the reactor, in which methanol droplets were present in dispersed form. This was clearly identifiable with reference to the speed of ascent of the droplets of the disperse phase. At a mean droplet diameter of approx. 5 mm, a speed of ascent of approx. 20 mm/s was measured, which was thus significantly greater than the mean superficial velocity of the reaction mixture, and so it was concluded from this that the droplets are methanol which, under the experimental conditions, has a significantly lower density than the oil.

In the reaction product, after removal of the methanol, an acid content of 0.19% by weight was determined. A conversion based on the free fatty acids of only 64.2% was achieved.

Overall, a total fatty acid conversion of 98.9% is calculated.

The invention claimed is:

1. A process for reducing the content of free fatty acids in fats and/or oils comprising the steps of:
   1) reacting the free fatty acids in said fats and/or oils with alcohols at temperatures between 60 and 120° C. using acidic, heterogeneous ion exchange resin catalysts, wherein said acidic, heterogeneous ion exchange resin catalysts are present in a continuous alcoholic phase in which said free fatty acids are present in finely dispersed form and wherein the reaction zone in which the foregoing reaction is performed is flowed through vertically from the top downward, and
   2) optionally removing water, and optionally alcohol at least partly together with it, and
   3) optionally further reacting the remaining free fatty acids in the product of step 1) or optionally 2) with alcohols at temperatures between 60 and 120° C. using acidic, heterogeneous ion exchange resin catalysts,
   wherein in step 1) and optionally in step 3), a continuous alcoholic phase is present at the upper end of the reaction zone.

2. The process according to claim 1, wherein the reaction of the free fatty acids in step 1) is followed by removal of water.

3. The process according to claim 1, wherein the reaction of the free fatty acids in step 1) is followed by removal of water and alcohol.

4. The process according to claim 2, wherein the removal of the water is carried out selectively, with the aid of a membrane.

5. The process according to claim 3, wherein the water is removed together with a portion or the entirety of the alcohol by evaporation.

6. The process according to claim 1, wherein the reaction of the free fatty acids in step 1) is followed by a performance of a further reaction in step 3) of the free fatty acids with alcohols at temperatures between 60 and 120° C. using acidic, heterogeneous ion exchange resin catalysts.

7. The process according to claim 2, wherein the removal in step 2) is followed by a performance of a further reaction in step 3) of the free fatty acids with alcohols at temperatures between 60 and 120° C. using acidic, heterogeneous ion exchange resin catalysts.

8. The process according to claim 6, wherein, in the course of the reaction in step 3) in the reaction zone, the acidic, heterogeneous ion exchange resin catalyst is present in a continuous alcoholic phase in which the free fatty acids are present in finely dispersed form.

9. The process according to claim 1, wherein the reaction and/or further reaction is carried out at temperatures between 80 and 95° C.

10. The process according to claim 6, wherein the further reaction is preceded by addition of additional alcohol.

11. The process according to claim 1 wherein step 3) is performed more than once.

12. The process according to claim 1 wherein the alcohol is added to said fats and/or oils in step 1) in a molar ratio of 5 to 40.

13. The process according to claim 1, wherein the acidic, heterogeneous ion exchange resin catalysts are strongly acidic polymeric macroporous resins with free sulphonic acid groups.

14. The process according to claim 1 wherein a catalyst hourly space velocity of $$0.1 \text{ to } 10 \ \frac{\text{kg}}{\text{kg} \cdot \text{h}},$$

is present.

15. The process according to claim 1 wherein the sequence of steps 2) and 3) are performed more than once.

16. The process according to claim 12 wherein the alcohol is added to said fats and/or oils in step 1) in a molar ratio of 5 to 20.

17. The process according to claim 16 wherein the alcohol is added to said fats and/or oils in step 1) in a molar ratio of 10 to 20.

18. The process according to claim 14 wherein the catalyst hourly space velocity is $$0.15 \text{ to } 5 \ \frac{\text{kg}}{\text{kg} \cdot \text{h}}.$$

19. The process according to claim 18 wherein the catalyst hourly space velocity is $$0.2 \text{ to } 3 \ \frac{\text{kg}}{\text{kg} \cdot \text{h}}.$$

* * * * *